(12) United States Patent
Araki

(10) Patent No.: US 7,670,283 B2
(45) Date of Patent: Mar. 2, 2010

(54) ENDOSCOPE INFORMATION SYSTEM

(75) Inventor: Hiroyuki Araki, Tokyo (JP)

(73) Assignee: Olympus Corporation, Tokyo (JP)

(*) Notice: Subject to any disclaimer, the term of this patent is extended or adjusted under 35 U.S.C. 154(b) by 1369 days.

(21) Appl. No.: 10/693,432

(22) Filed: Oct. 24, 2003

(65) Prior Publication Data

US 2004/0107113 A1 Jun. 3, 2004

(30) Foreign Application Priority Data

Nov. 28, 2002 (JP) ............................. 2002-344900

(51) Int. Cl.
*A61B 1/00* (2006.01)
(52) U.S. Cl. ...................................... 600/117; 600/118
(58) Field of Classification Search ................. 600/117, 600/118; 348/65, 72, 74
See application file for complete search history.

(56) References Cited

U.S. PATENT DOCUMENTS

| | | | | |
|---|---|---|---|---|
| 4,539,632 A * | 9/1985 | Hansen et al. | ................. | 700/14 |
| 4,876,632 A * | 10/1989 | Osterhout et al. | ........... | 362/183 |
| 4,996,975 A * | 3/1991 | Nakamura | ................... | 600/118 |
| 5,830,121 A | 11/1998 | Enomoto et al. | | |
| 6,307,332 B1 * | 10/2001 | Noguchi et al. | ............. | 315/362 |
| 6,322,496 B1 * | 11/2001 | Iida et al. | ..................... | 600/118 |
| 6,436,032 B1 * | 8/2002 | Eto et al. | ..................... | 600/117 |
| 2002/0095348 A1 | 7/2002 | Hiroshige et al. | | |
| 2003/0060682 A1 * | 3/2003 | Handa et al. | ................ | 600/178 |

FOREIGN PATENT DOCUMENTS

| | | |
|---|---|---|
| EP | 1 153 568 | 11/2001 |
| EP | 1 155 654 | 11/2001 |
| JP | 7-171089 | 7/1995 |
| JP | 7-171090 | 7/1995 |
| JP | 2000-126124 | 5/2000 |
| JP | 2001-46326 | 2/2001 |
| JP | 2002-73615 | 3/2002 |
| JP | 2002-183547 | 6/2002 |
| WO | WO 99/66444 | 12/1999 |

OTHER PUBLICATIONS

European Office Action, dated May 30, 2005.

* cited by examiner

*Primary Examiner*—John P Leubecker
(74) *Attorney, Agent, or Firm*—Scully, Scott, Murphy & Presser, P.C.

(57) ABSTRACT

A history information obtaining unit obtains information about a use history of an endoscope. An estimating unit makes an estimation of a secular change in the endoscope from its use start until the present time based on this information. A displaying unit displays a ratio of a result of the estimation made by the estimating unit to the degree of the secular change, which is preset for the endoscope.

11 Claims, 10 Drawing Sheets

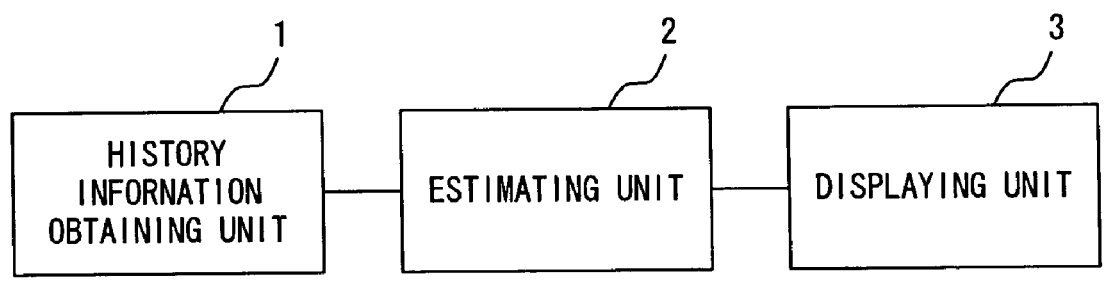
F I G. 1

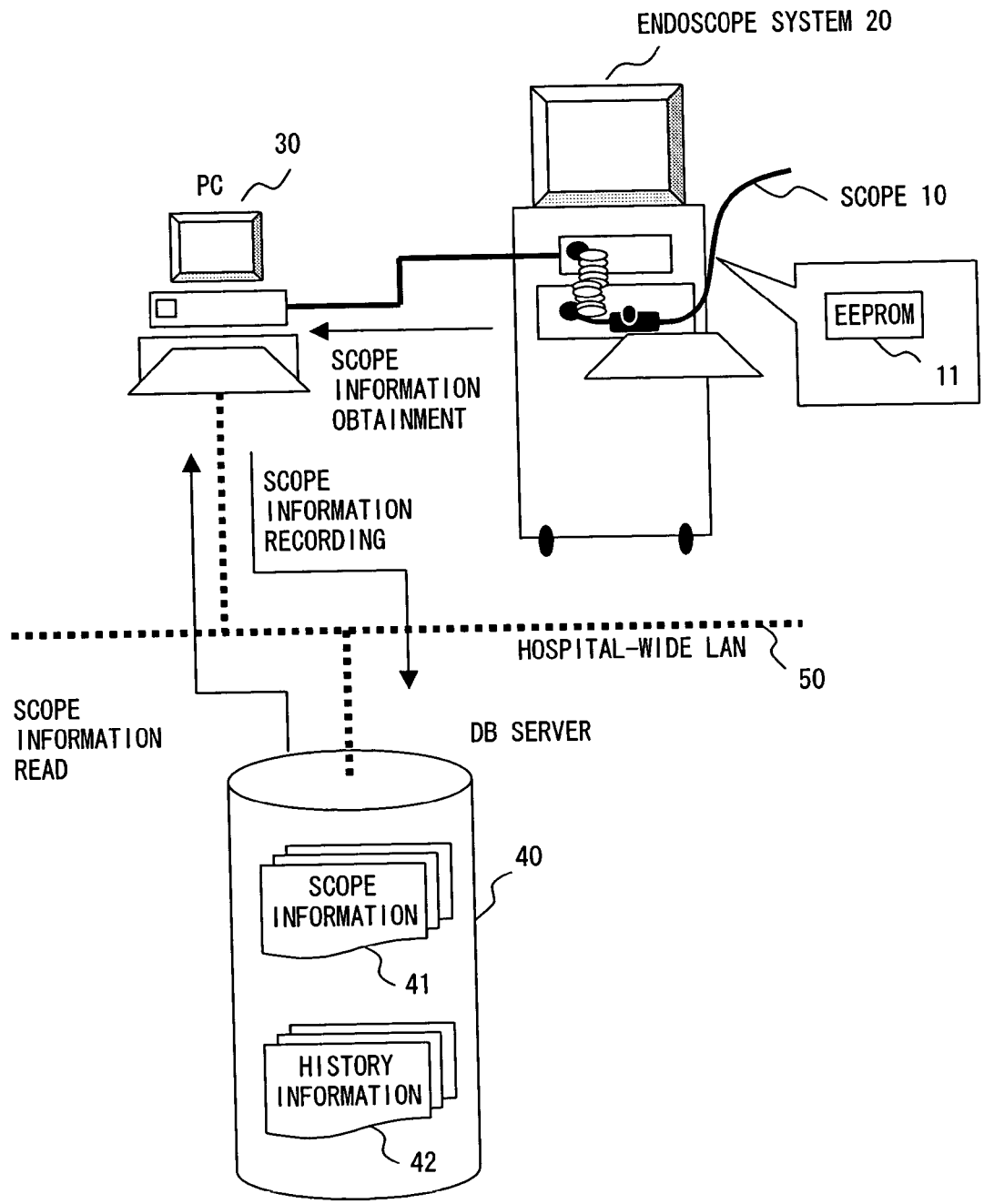
F I G. 2

| SCOPE TYPE NAME | SCOPE ID | USE START DATE | NUMBER OF USE TIMES | USE TIME |
|---|---|---|---|---|
| | | | | |

| USE DATE | USE START TIME | USER | PATIENT ID | PATIENT NAME | EXAMINATION ITEM | CLEANED/NOT CLEANED |
|---|---|---|---|---|---|---|
| | | | | | | |

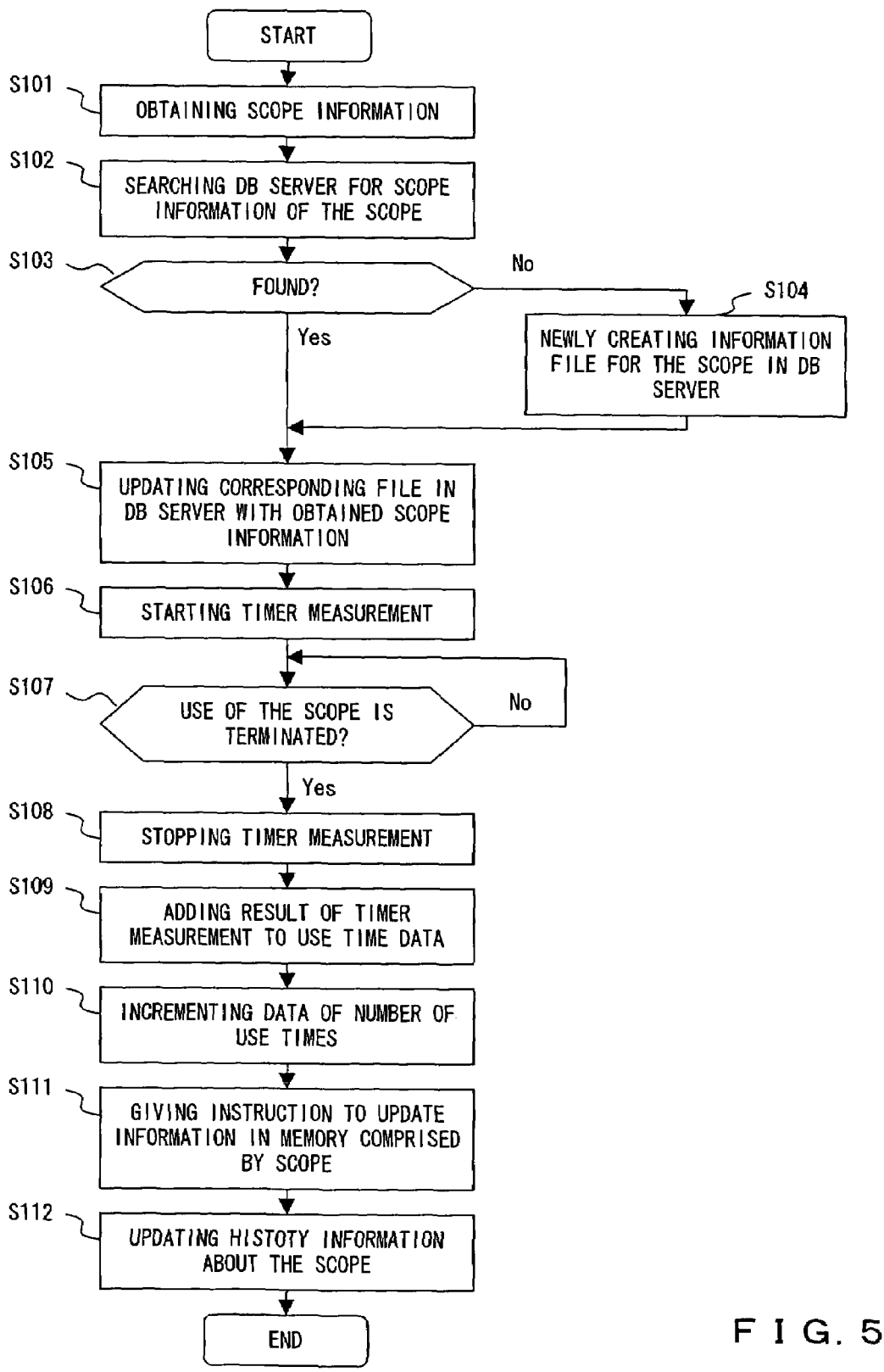
F I G. 5

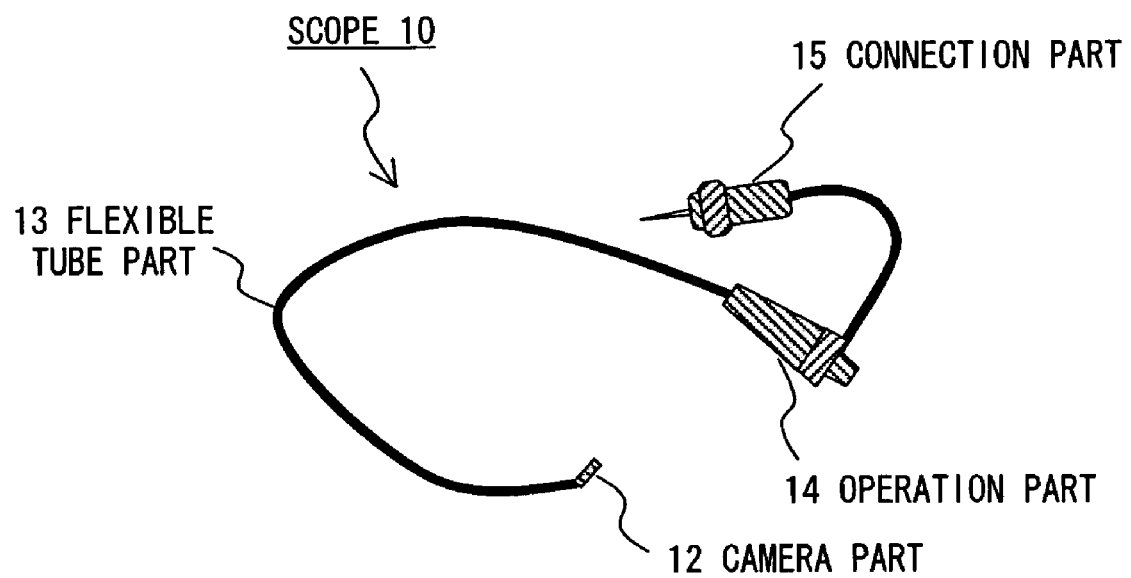
F I G. 7

STATISTICS/HISTORY

| | SCOPE LIST | | | UPDATE | | CLASSIFICATION: ALL ARE DISPLAYED | | | | PRINT LIST |
|---|---|---|---|---|---|---|---|---|---|---|
| | SCOPE NO. | CLASSI-FICATION | SCOPE NAME | SCOPE ID | USE START DATE | NUMBER OF USE TIMES | USE TIME (MINUTES) | CURRENT STATE | LIFE | |
| DAILY REPORT | 01 | GIF | GIF-H260 | 100000001 | 2001/08/20 | 10 | 125 | CLEANED | ●●●●●●●○○○ | |
| MONTHLY REPORT | 02 | GIF | GIF-GX240 | 100000002 | 2001/08/20 | 30 | 300 | CLEANED | ●●●●●●●●○○ | |
| | 03 | GIF | GIF-KQ240 | 100000003 | 2001/08/20 | 15 | 154 | CLEANED | ●●●●●●●○○○ | |
| PERFORMANCE LIST OUTPUT | 04 | GIF | GIF-XK240 | 100000004 | 2001/08/20 | 3 | 37 | CLEANED | ●●●●●●●●○○ | |
| | 05 | CF | CF-Q240A1 | 200000001 | 2001/08/20 | 5 | 100 | CLEANED | ●●●●●●●●○○ | |
| TABLE FILE OUTPUT | 06 | CF | CF-24001 | 200000002 | 2001/08/20 | 10 | 120 | NOT CLEANED | ●●●●●●●●○○ | |
| | 07 | EUS | CF-UNQ240 | 300000001 | 2001/08/20 | 1 | 15 | NOT CLEANED | ●●●●●●●○○○ | |
| CLEANING HISTORY | 08 | ERCP | TJF-240 | 400000001 | 2001/08/20 | 3 | 45 | NOT CLEANED | ●●●●●●●●○○ | |
| SCOPE HISTORY | 09 | BF | BF-240 | 500000001 | 2001/08/20 | 2 | 53 | NOT CLEANED | ●●○○ | |
| FOLLOW-UP SEARCH | | | | | | | | | | |

LOGIN USER:

LOGOUT

F I G. 8

SCOPE USE HISTORY

■ SCOPE INFORMATION

SCOPE TYPE NAME :
· GIF-H260

SCOPE ID :
· 10000001

USE START DATE :
· 2002/08/28

NUMBER OF USE TIMES :
· 10 TIMES

USE TIME (MINUTES) :
· 125 MINUTES

SCOPE LIFE ○ ◌ ● ●

■ USE HISTORY

DISPLAY DURATION : 2002/08/29～2002/08/30    USER : ALL

| USE DATE | USE START TIME | USER | PATIENT ID | PATIENT NAME | EXAMINATION ITEM | CLEANED/ NOT CLEANED |
|---|---|---|---|---|---|---|
| 2002.08.29 | 09:00:00 | OLYMPUS TARO | 00140481 | OLYMPUS ICIRO | COLONOSCOPY | CLEANED |
| 2002.08.29 | 09:30:00 | OLYMPUS TARO | 00000001 | OLYMPUS JIRO | COLONOSCOPY | CLEANED |
| 2002.08.30 | 11:35:30 | OLYMPUS TARO | 11112222 | OLYMPUS SABURO | ERCP | CLEANED |
| 2002.08.30 | 14:10:00 | OLYMPUS TARO | 99999999 | OLYMPUS SHIRO | UPPER PORTION EMR | CLEANED |

BACK TO LIST                                   LOGIN USER

FIG. 9

ENDOSCOPE INFORMATION SYSTEM

CROSS REFERENCE TO RELATED APPLICATION

This application is based upon and claims the benefit of priority from the prior Japanese Application No. 2002-344900, filed Nov. 28, 2002, the entire contents of which are incorporated herein by reference.

BACKGROUND OF THE INVENTION

1. Field of the Invention

The present invention relates to a technique for assisting in a service of an endoscopic examination performed in a medical institution, etc., and more particularly, to a technique for managing the use of an endoscope.

2. Description of the Related Art

As techniques for assisting in a service of an endoscopic examination, the techniques disclosed by Japanese Patent Publications Nos. 2001-46326 and 2002-73615 are known.

Among these techniques, Japanese Patent Publication No. 2001-46326 discloses a system managing the use status or the cleaning state of an endoscope part in an endoscope system. This system has a function for displaying the recommended maintenance timing of an endoscope by year and month for each endoscope. The year and month of the recommended maintenance timing is decided based on the number of times that an examination is performed with the endoscope, the number of times that the endoscope is inserted/removed in/from an endoscope system, the number of times (the number of releases) that an endoscopic image is recorded with the endoscope, and an accumulated use time of the endoscope. Accordingly, as the use frequency of the endoscope significantly changes, its year-and-month display constantly changes.

SUMMARY OF THE INVENTION

An endoscope information system as one aspect of the present invention is configured to comprise a history information obtaining unit obtaining information about a use history of an endoscope, an estimating unit making an estimation of a secular change in the endoscope from its use start until the present time based on the obtained information, and a displaying unit displaying the ratio of a result of the estimation to the degree of the secular change, which is preset for the endoscope.

In the above described configuration, preferably, the degree of the secular change, which is preset for the endoscope, may be a degree at which maintenance is recommended to be performed for the endoscope.

Additionally, preferably, the information about the use history may indicate at least either of the use time and the number of use times of the endoscope.

Furthermore, preferably, the information about the use history may be stored in a scope storing unit comprised by the endoscope.

Still further, preferably, the system may be configured so that scope identification information for identifying the endoscope is further stored in the scope storing unit, and the system further comprises a use history storing unit storing the information about the use history of each of a plurality of endoscopes in association with the scope identification information.

Still further, preferably, the displaying unit may display the ratio of the result of the estimation as a figure.

Still further, preferably, the displaying unit may individually display the ratio of the result of the estimation of the plurality of endoscopes for each of the plurality of endoscopes.

Still further, preferably, the displaying unit may display the ratio of the result of the estimation for each of the plurality of endoscopes.

BRIEF DESCRIPTION OF THE DRAWINGS

The present invention will be more apparent from the following detailed description when the accompanying drawings are referenced.

FIG. 1 shows the principle configuration of a system implementing the present invention;

FIG. 2 shows a specific configuration of the system implementing the present invention;

FIG. 4A shows the data structure of scope information;

FIG. 4B shows the data structure of history information;

FIG. 5 is a flowchart showing the contents of a scope information obtainment/update process;

FIG. 7 explains a secular change in a scope;

FIG. 8 exemplifies a scope list screen;

FIG. 9 exemplifies a scope use history screen; and

DESCRIPTION OF THE PREFERRED EMBODIMENTS

Figure 3:
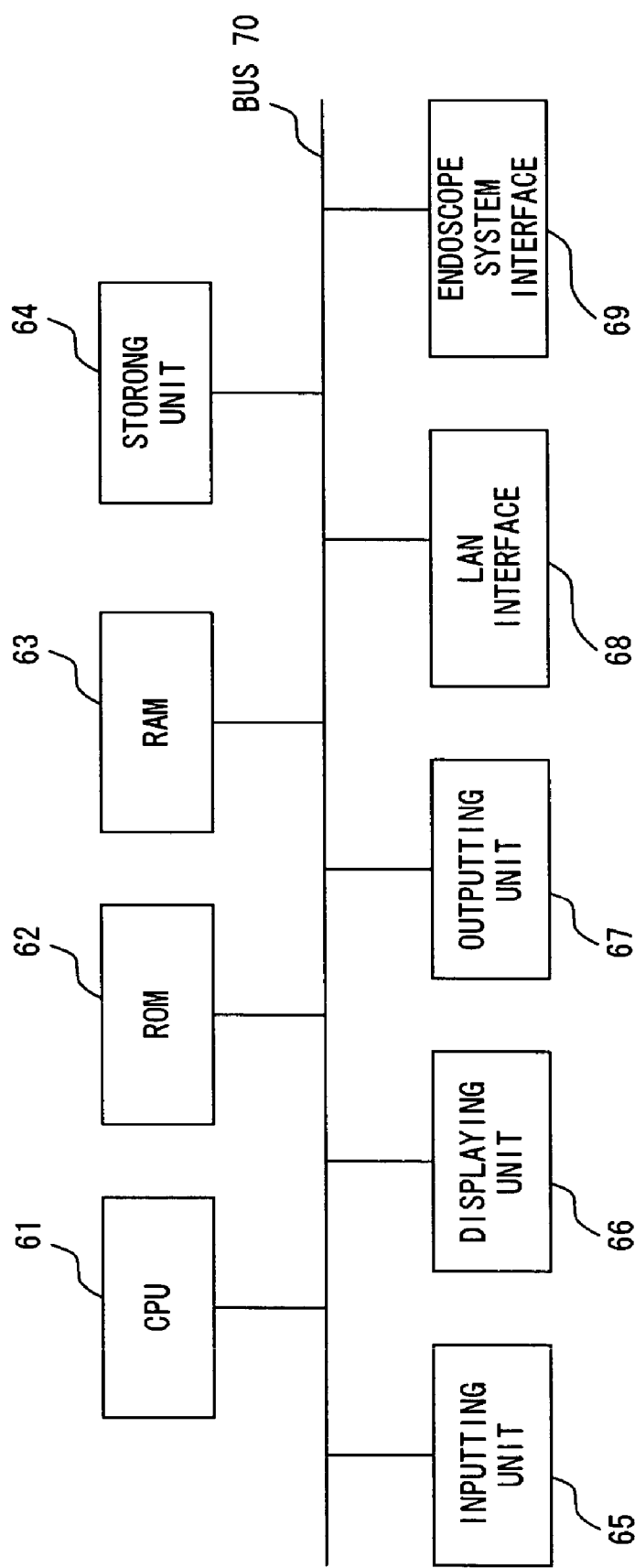
FIG. 3 shows the configuration of a PC and a DB server, which are shown in FIG. 2.

First of all, FIG. 1 is described. This figure shows the principle configuration of an endoscope information system implementing the present invention.

A history information obtaining unit 1 obtains information about a use history of an endoscope.

An estimating unit 2 makes an estimation of a secular change in the endoscope from its use start until the present time based on this information.

A displaying unit 3 displays the ratio of a result of the estimation made by the estimating unit 2 to the degree of the secular change, which is preset for the endoscope.

Here, the degree of the secular change, which is preset for the endoscope, may be a degree at which maintenance is recommended to be performed for the endoscope.

With the above described configuration, the result of the estimation of the secular change from the start until the present time in an endoscope which changes monotonously is presented with the ratio to the degree of the secular change in the endoscope. As a result, a margin remaining until the secular change in the endoscope becomes a predetermined degree can be suitably provided to a user of the endoscope.

In the above described endoscope information system implementing the present invention, the information about the use history, which is obtained by the history information obtaining unit 1, may indicate at least either or both of the use time and the number of use times of an endoscope.

With this configuration, the estimating unit 2 can make an estimation of the secular change in an endoscope from its use start until the present time based on either or both of the use time and the number of use times of the endoscope.

Additionally, in the above described endoscope information system implementing the present invention, the information about the use history, which is obtained by the history information obtaining unit 1, may be information stored in a scope storing unit comprised by the endoscope.

This configuration facilitates the management of a correspondence between an endoscope and information about its use history.

Here, the system may be configured so that scope identification information for identifying an endoscope is further stored in the scope storing unit, and the endoscope information system further comprises a use history storing unit storing the information about the use history of each of a plurality of endoscopes in association with the scope identification information.

With this configuration, a margin remaining until a secular change in an endoscope becomes a predetermined degree can be provided to a user of the endoscope even if the endoscope is removed from the endoscope information system.

Additionally, in the above described endoscope information system implementing the present invention, the displaying unit 3 may be configured to display the above described ratio of the result of the estimation made by the estimating unit 2 as a figure.

With this configuration, a margin remaining until a secular change in an endoscope becomes a predetermined degree is presented as a figure in an analog manner, so that the degree of the remaining margin can be quickly grasped.

Furthermore, in the above described endoscope information system implementing the present invention, the displaying unit 3 may be configured to individually display the aforementioned ratio of the result of the estimation of a plurality of endoscopes for each of the plurality of endoscopes.

With this configuration, a user of an endoscope an quickly recognize the above described ratio of the result of the estimation of the particular endoscope.

Additionally, in the above described endoscope information system implementing the present invention, the displaying unit 3 may be configured to list and display the aforementioned ratio of the result of the estimation of each of a plurality of endoscopes.

With this configuration, a user of an endoscope can altogether recognize the above described ratio of the result of the estimation of a plurality of endoscopes.

FIG. 2 is described next. This figure shows a specific configuration of the system implementing the present invention. This system is assumed to be installed within a hospital.

A scope 10 is an endoscope, and comprises an EEPROM (Electrically Erasable and Programmable Read-Only Memory: a programmable ROM that can be erased electrically) 11, which is intended to store scope information to be described later.

An endoscope system 20 is a system controlling the obtainment/display/output of an image by controlling the scope 10. Particularly, the endoscope system 20 writes and reads data stored in the EEPROM 11 comprised by the scope 10.

A PC 30 is a personal computer which is respectively connected to the endoscope system 20 directly, and to a DB server 40 via a hospital-wide LAN (Local Area Network) 50 installed within a hospital. The PC 30 is used to give an instruction of a data operation to the DB server 40 based on data that the endoscope system 20 reads from the EEPROM 11, or to give an instruction of an update of data stored in the EEPROM 11. The PC 30 also makes a display of scope life information of the scope 10, which will be described later.

The DB (database) server 40 stores data such as scope information 41, history information 42, etc., which will be described later, and performs a data operation for its stored data based on an instruction transmitted from the PC 30.

FIG. 3 is described next. This figure shows the configuration of the PC 30 and the DB server 40, which are shown in FIG. 2.

The device shown in FIG. 3 is configured by interconnecting a CPU 61, a ROM 62, a RAM 63, a storing unit 64, an inputting unit 65, a displaying unit 66, an outputting unit 67, a LAN interface 68, and an endoscope system interface 69 via a bus 70, and these constituent elements can mutually exchange data under the control of the CPU 61.

The CPU (Central Processing Unit) 61 is a central processing unit which governs the operation control of the entire device shown in FIG. 3

The ROM (Read-Only Memory) 62 is a memory in which a basic control program executed by the CPU 61 is prestored. The CPU 61 executes this basic control program when the device shown in FIG. 3 is started up, whereby the basic control of the operations of the entire device is performed by the CPU 61.

The RAM (Random Access Memory) 63 is a memory used as a working memory when the CPU 61 executes various types of control programs, and is a memory which also functions as a main memory used as a temporary storage area of various types of data depending on need.

The storing unit 64 is configured by comprising, for example, an HDD (Hard Disk Drive). If the device shown in FIG. 3 is used as the PC 30, a control program for causing the CPU 61 to execute a scope information obtainment/update process and a scope life display process, which will be described later, is prestored in the storing unit 64. Or, if the device shown in FIG. 3 is used as the DB server 40, the storing unit 64 functions as a data storing device storing various types of data such as the scope information 41, the history information 42, etc., which will be described later, and at the same time, the storing unit 64 prestores a control program for causing the CPU 61 to execute a data operation process for this database according to instructions of various types of data operations, which are transmitted from the PC 30.

The inputting unit 65 is intended to receive an external input, and to pass the contents of the input to the CPU 61, and comprises an input device such as a keyboard, a mouse, etc. for receiving an instruction from an operator who operates this device. Additionally, the inputting unit 65 is configured by comprising a reading device of a portable storage medium such as an FD (Flexible Disk), a CD-ROM (Compact Disc-ROM), a DVD-ROM (Digital Versatile Disc-ROM), an MO (Magneto-Optic) disk, etc., depending on need.

The displaying unit 66 is intended to display various types of information according to an instruction from the CPU 61, and configured by comprising, for example, a CRT (Cathode Ray Tube) or an LCD (Liquid Crystal Display).

The outputting unit 67 is intended to output various types of information according to an instruction from the CPU 61, and is, for example, a printer device for printing the contents of a display made on the displaying unit 66 unchanged on paper, or the like.

The LAN interface 68 connects this device to the hospital-wide LAN 50, and manages a communication made when a data exchange is made between the PC 30 and the DB server 40.

The endoscope system interface 69 connects the PC 30 to the endoscope system 20, and manages a communication made when a data exchange is made in the case where the device shown in FIG. 3 is the PC 30. If the device shown in FIG. 3 is used as the DB server 40, this endoscope system interface 69 is unnecessary.

The device shown in FIG. 3 is normally comprised by a computer system if the system has a standard hardware configuration. Therefore, the PC 30 or the DB server 40 can be also configured by diverting such a computer system.

FIGS. 4A and 4B are described next. These figures show the data structures of various types of data handled by the system shown in FIG. 2. FIG. 4A shows the data structure of scope information, whereas FIG. 4B shows the data structure of history information.

The scope information 41 shown in FIG. 4A is information about a scope 10. The scope information 41 includes various types of data such as a "scope type name" for identifying the type of a scope 10, a "scope ID" that is an identifier assigned to identify the scope 10 from others, "use start date" of the scope 10, "the number of use times" of the scope 10 after the use start, "use time" of the scope 10 after the use start, etc.

The scope information 41 is originally information stored in the EEPROM 11 comprised by the scope 10. When the scope 10 is connected to the endoscope system 20, the scope information 41 is read by the endoscope system 20 and transmitted to the PC30. The PC 30 that obtains the scope information 41 gives an instruction of a data operation to the DB server 40, and makes the DB server 40 update its stored scope information 41. At this time, if the instruction of a data operation for a new scope 10 yet to be stored is given from the PC 30, the DB server 40 stores its scope information 41, creates a file for storing the history information 42 about the new scope 10, and stores the history information 42 in the created file.

The history information 42 shown in FIG. 4B is information indicating the use history of a scope 10. The history information 42 is created as a separate data file for each scope ID which is assigned to identify a scope 10. Each time a scope 10 is used, its history is added to a data file by 1 record. In respective fields of the record, "use date" indicating year, month and day on which a scope 10 is used, a "use start time" indicating a time at which the use of the scope 10 is started, a "user" indicating the name of a person who performs an endoscopic examination with the scope 10, a "patient ID" which is an identifier assigned to identify a patient and indicates a person for whom the endoscopic examination is to be performed, a "patient name" indicating the name of the patient, an "examination item" indicating the name of an examination item in the performed endoscopic examination, and "cleaned/not cleaned" indicating whether or not the scope 10 is cleaned after being used.

Note that the scope information 41 and the history information 42 may include data in addition to the above described data.

FIG. 5 is described next. This figure is a flowchart showing the contents of a scope information obtainment/update process. This process is a process for updating the scope information 41 of a scope 10 stored in the EEPROM 11 of the scope 10, and for making the scope information 41 about the scope 10, which is stored in the DB server 40, match the scope information stored in the EEPROM 11, when the scope 10 is used.

The process shown in FIG. 5 is a process executed by the CPU 61 of the PC 30. The CPU 61 implements this process by executing a control program stored in the storing unit 64 of the PC 30. Additionally, this process is started when a notification indicating that the scope 10 is inserted in the endoscope system 20 is transmitted from the endoscope system 20 to the PC 30, and the CPU 61 of the PC 30 detects the receipt of this notification.

Firstly, in S101, a process for instructing the endoscope system 20 to read the scope information 41 stored in the EEPROM 11 of the scope 10, and for obtaining the read scope information 41 from the endoscope system 20 is executed.

In S102, a process for instructing the DB server 40 to search for the scope information 41 about the scope 10 is executed. The DB server 40 searches the storing unit 64 of the DB server 40 according to this instruction, and returns information indicating whether or not the instructed scope information 41 exists to the PC 30 as a result of the search.

In S103, contents of the result returned from the DB server 40 are examined, and whether or not the instructed scope information 41 is found is determined. Only if the instructed scope information 41 is not found as a result (if the result of the determination process in S103 is "NO"), a process for giving an instruction to the DB server 40, and for newly creating an information file of the scope 10, namely, a data file for storing the scope information 41 and the history information 42 of the scope 10 in the storing unit 64 of the DB server 40 is executed in S104.

In S105, a process for transmitting to the DB server 40 the scope information 41 obtained with the above described process of S101 is executed. In the DB server 40, a data update process for making the scope information 41 about the scope, which is stored in the storing unit 64, match the transmitted data is executed.

In S106, a process for resetting and activating a timer that is constructed by executing the control program in the CPU 61 and measures the elapse of time is executed, so that the measurement of the use time of the scope 10 at this time is started.

Thereafter, a determination process in S107 is repeated until the PC 30 detects the receipt of a notification indicating that the use of the scope 10 is terminated from the endoscope system 20.

In S108, a process for stopping the measurement operation of the timer activated with the above described process of S106 is executed.

In S109, a process for adding the measurement time of the timer stopped with the process of the preceding step, namely, the use time of the scope 10 at this time to the value indicated by the data of the "use time" in the scope information 41 obtained with the above described process of S101 to update the data is executed.

In S110, a process for incrementing by the value indicated by the data of "the number of use times" in the scope information 41 obtained with the above described process of S101 to update the data is executed.

In S111, a process for transmitting to the endoscope system 20 the data of the "use time" and "the number of use times", which are updated with the above described processes of S109 and S110, and for updating these pieces of data in the scope information 41 stored in the EEPROM 11 of the scope 10 is executed. After the endoscope system 20 updates the scope information 41 in the EEPROM 11, it permits the removal of the scope 10 from the endoscope system 20.

In S112, a process for transmitting the data of the "use time" and "the number of use times", which are updated with the above described processes of S109 and S110, to the DB server 40, and for updating these pieces of data in the scope information 41 about the scope 10 stored in the storing unit 64 of the DB server 40 is executed. Then, the scope information obtainment/update process is terminated.

The processes up to this point are the scope information obtainment/update process.

Figure 6:
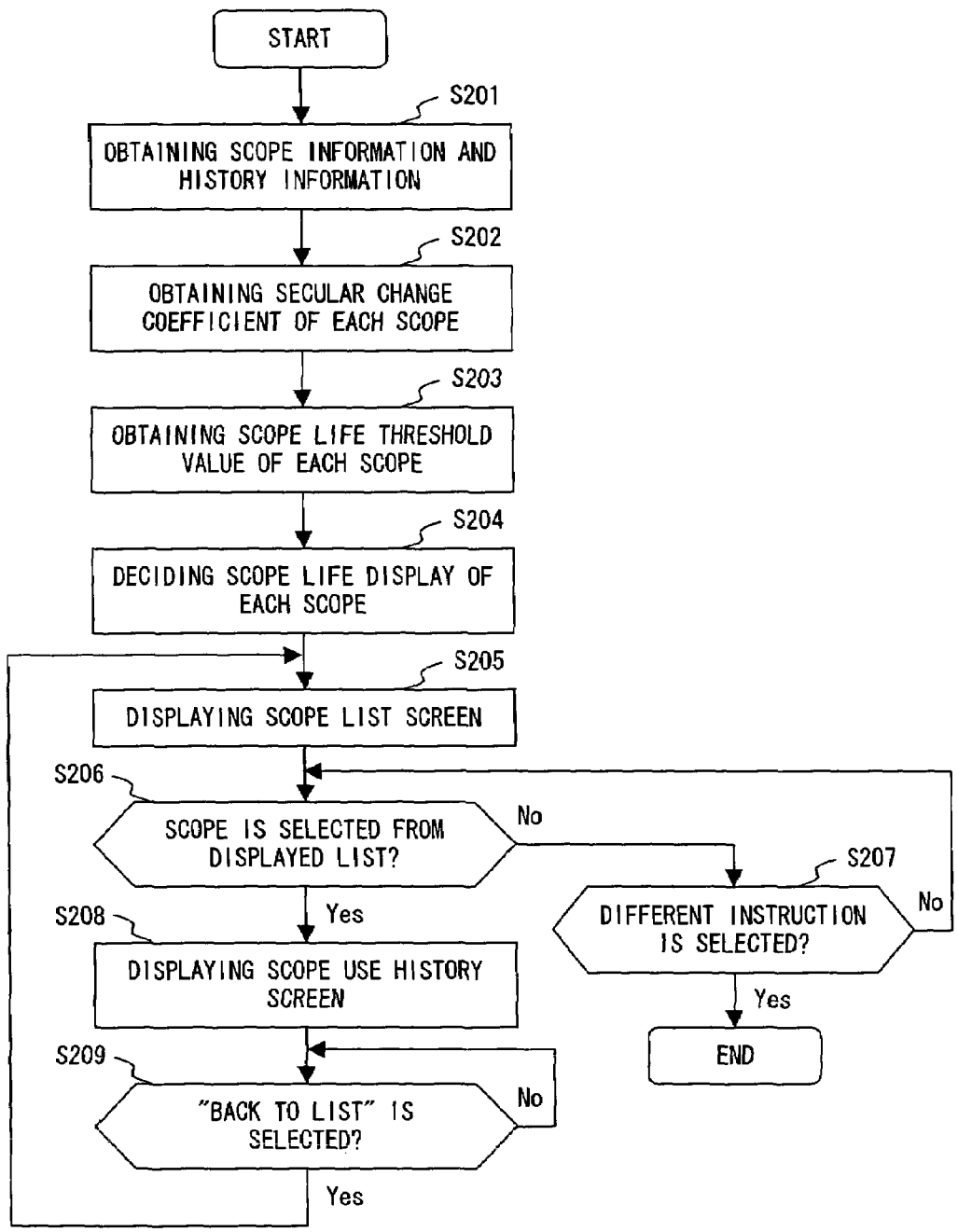
FIG. 6 is a flowchart showing the contents of a scope life display process.

FIG. 6 is described next. FIG. 6 is a flowchart showing the contents of a scope life display process. This process is a process for obtaining a scope life of each scope 10 whose scope information 41 is stored in the DB server 40, and for displaying the scope life on the displaying unit 66 of the PC 30.

Here, the scope life is described. The scope life of a scope 10 indicates the ratio of a secular change in the scope 10 from its use start (or after the immediately preceding maintenance) until the present time to a secular change amount for which maintenance is recommended to be performed for the scope 10. In this preferred embodiment, the secular change amount in the scope 10 from its use start until the present time is estimated based on the information about the use history of the scope 10, such as the use time and the number of use times, and the ratio of the secular change preset for the scope 10, namely, the ratio of the result of the estimation to the secular change amount for which maintenance is recommended to be performed for the scope 10 is visually displayed on the displaying unit 66 of the PC 30 as a figure, so that the scope life is presented to a user.

The process shown in FIG. 6 is a process executed by the CPU 61 of the PC 30. The CPU 61 implements this process by executing a control program stored in the storing unit 64 of the PC 30. Additionally, this process is started when the CPU 61 of the PC 30 detects that an input indicating an instruction to make the displaying unit 66 of the PC 30 display a scope history is made to the inputting unit 65 of the PC 30.

Firstly, in S201, a process for giving an instruction to transmit to the PC 30 all pieces of scope information 41 stored in the storing unit 64 of the DB server 40, and the history information 42 corresponding to all pieces of the scope information 41 to the DB server 40 is executed. In accordance with this instruction, the DB server 40 transmits the scope information 41 and the history information 42, which are read from the storing unit 64, to the PC 30.

In S202, a process for reading all of secular change coefficients for the same type as scopes 10 corresponding to the scope information 41 obtained with the process of the preceding step among secular change coefficients of respective scopes, which are prestored in the storing unit 64 of the PC 30, is executed.

Here, a method for estimating a secular change in a scope from its use start until the present time, and a secular change coefficient of a scope are described. In this preferred embodiment, a secular change amount N of a scope 10 shown in FIG. 7 is calculated with the following equation.

$$N = P1(\alpha + \beta + \gamma + \Delta) + P2(\epsilon + \zeta + \eta + \theta) + C$$

In the above provided equation, P1 is the total use time from the use start until the present time, P2 is the total number of use times from the use start until the present time, and P1 and P2 are indicated by the scope information 41 about the scope 10. Additionally, $\alpha$, $\beta$, $\gamma$, and $\Delta$ are secular change coefficients indicating the number of occurrences of faults per unit number of use times, and $\epsilon$, $\zeta$, $\eta$, and $\theta$ are secular change coefficients indicating the number of occurrences of faults per unit number of use times. Additionally, $\alpha$ and $\epsilon$ are the coefficients for a camera part 12, $\beta$ and $\zeta$ are the coefficients for a flexible tube part 13, $\gamma$ and $\eta$ are the coefficients for an operation part 14, and $\Delta$ and $\theta$ are the coefficients for a connection part 15. Furthermore, C is a secular change coefficient, which is a constant. These secular change coefficients are statistically calculated, for example, from the numbers of occurrences of faults of scopes of the same type.

Note that a method other than the above described one may be adopted for the calculation of the secular change amount of the scope 10.

Turning back to the description of FIG. 6. In S203, a process for obtaining a scope life threshold value for each scope is executed. In the following S204, a process for deciding a scope life display of each scope is executed. In S205, a process for making the displaying unit 66 of the PC 30 display a scope list screen is executed.

Here, FIG. 8 is described. This figure exemplifies a scope list screen. This scope list screen lists and displays part of all pieces of scope information 41 and history information 42, which are stored in the storing unit 64 of the DB server 40, and a scope life display of each scope.

With reference to FIG. 8, the scope information 41 of 9 scopes are proved to be stored in the storing unit 64 of the DB server 40. Additionally, contents of respective pieces of data such as a "scope name" (namely, a "scope type name"), a "scope ID", "use start date", "the number of use times", and "use time", which are the scope information 41, and contents of data of "cleaned/not cleaned", which is the history information 42, are proved to be displayed on the scope list screen shown in FIG. 8. On the scope list screen, "scope No." is a number assigned in descending order for the sake of convenience when information about each scope is displayed on the scope list screen. Additionally, "classification" indicates the classification of the type of a scope. This information is obtained, for example, by referencing a table not shown, which is stored in the storing unit 64 of the DB server 40, and indicates the correspondence between the type name of a scope and the classification of the type of the scope.

At the right end of each line on the scope list screen shown in FIG. 8, the scope life of a scope indicated by a corresponding line is displayed. In this preferred embodiment, the scope life is indicated by four circles arranged in a single horizontal line.

If a scope is yet to be used, all of the four circles are displayed as white circles. As the value of the secular change amount of the scope increases thereafter, only the leftmost circle first changes in an order of "white circle→shaded circle→black circle". After the leftmost circle becomes a black circle, the second circle from the leftmost one changes next in the order of "white circle→shaded circle→black circle" while the display of the black circle is being maintained. Thereafter, also the third and the fourth circles from the leftmost one change in a similar manner with an increase in the value of the secular change amount of the scope. When the value reaches the secular change amount for which maintenance is recommended to be performed, all of the four circles become black circles. Namely, as the display of the scope life, 9-step displays are made in total from a display of "white, white, white, white" to a display of "black, black, black, black".

The scope life threshold value obtained with the process of S203 is a threshold value for deciding the display of the scope life corresponding to the value of the secular change amount of a scope, which is calculated with the above described equation. Since the 9-step scope life displays are made in this preferred embodiment, 8 numerical values are prepared as scope life threshold values for respective types of a scope, and prestored, by way of example, in the storing unit 64 of the PC 30. In the process for deciding a scope life display in S204, a comparison is made to determine whether or not the value of the secular change amount of a scope is either larger or smaller than each scope life threshold value, and which of the 9-step scope life displays is made is decided based on a result of this comparison. In this preferred embodiment, the scope life display based on this decision is made on the scope list screen.

Turning back to the description of the flowchart shown in FIG. 6. In S206, it is determined whether or not an instruction to establish a selection of a particular scope is given to the inputting unit 65 of the PC 30 on the scope list screen that is displayed on the displaying unit 66 of the PC 30 with the above described process of S205. Here, if a result of this determination is "Yes", the process proceeds to S208. Or, if the result of the determination is "No", it is determined in S207 whether or not an instruction except for the scope selection is given to the inputting unit 65. Here, if a result of the determination is "Yes", this scope life display process is terminated, and a different process, which is executed according to the instruction, is started to be executed. Or, if the result of the determination process in S207 is "No", the process returns to S206, and the above described processes are repeated.

In S208, a process for making the displaying unit 66 of the PC 30 display a scope use history screen is executed.

Here, FIG. 9 is described. This figure exemplifies the scope use history screen. This scope use history screen indicates the scope information 41 about the scope according to the instruction detected in the process of S206, and its scope life display at the left side of the screen, and at the same time, it indicates the history information 42 about this scope, namely, various types of data such as "use date", "use start time", a "user", a "patient ID", a "patient name", an "examination item", and "cleaned/not cleaned".

In S209, it is determined whether or not an instruction to select a display of "back to list", which is provided at the left end of the bottom on the scope use history screen shown in FIG. 9, is given to the inputting unit 65 of the PC 30. Here, if a result of this determination is "Yes", the process returns to S205, and the above described processes are repeated. Or, if the result of this determination is "No", the process of S209 is repeated until the result of the determination becomes "Yes".

The processes up to this point are the scope life display process.

As described above, the aforementioned scope information obtainment/update process and scope life display process are executed by the CPU 61 of the PC 30, whereby an estimation of a secular change in a scope from its use start until the present time based on the information about a use history, and a display of the ratio of the result of the estimation to the degree of the secular change, which is preset for the scope and at which maintenance is recommended to be performed, are implemented.

In the scope life display in the above described preferred embodiment, circles change in the order of "white circle→shaded circle→black circle". Alternatively, display methods such as changing the color of a circle, changing the area or the shape of a graphic used as a scope life display, etc. can be adopted. Besides, as an alternative to a display in an analog manner as a figure, a display in a digital manner, such as a display of the ratio of the result of an estimation to the degree of a secular change, at which maintenance is recommended to be performed, as a percent with a numerical value may be made.

In the meantime, the present invention can be implemented also in a way such that a program for causing a computer to execute the above described scope information obtainment process/update process and scope life display process is created and stored onto a computer-readable storage medium, and the computer is made to read the program from the storage medium, and to execute the program.

Figure 10:
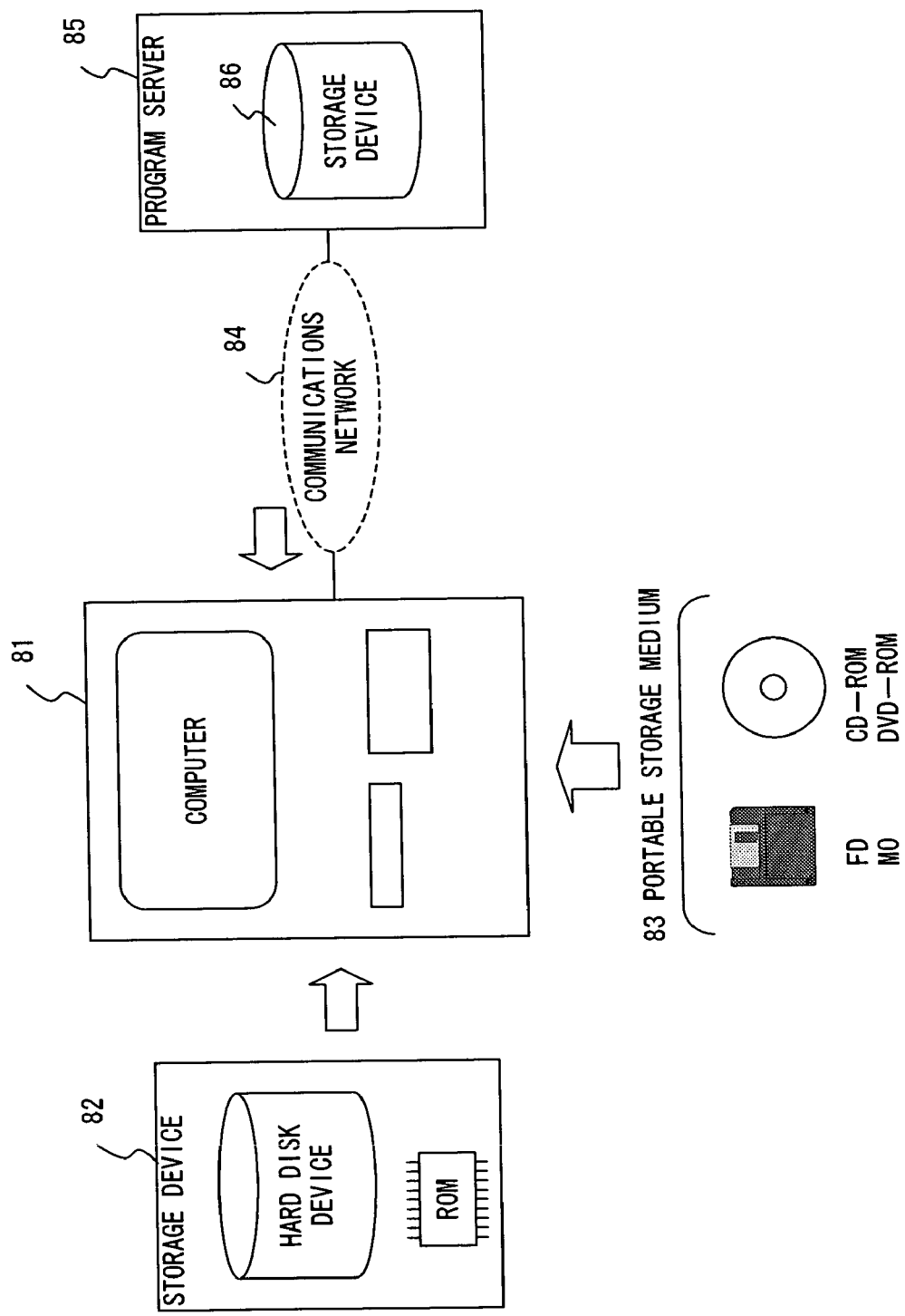
FIG. 10 exemplifies storage media from which a recorded control program can be read by a computer.

Storage media from which a recorded control program can be read by a computer are exemplified in FIG. 10. As such storage media, for example, a storage device 82 such as a ROM, a hard disk device, etc., which is included/externally attached in/to a computer 81, a portable storage medium 83 such as an FD (Flexible Disk), an MO (Magneto-Optic) disk, a CD-ROM, a DVD-ROM, etc., or the like are available.

Additionally, as a storage medium, a storage device 86 that is included/externally attached in/to a program server 85 connected to the computer 81 via a communications network 84 may be available. In such a case, a transmission signal, which is obtained by modulating a carrier wave with a control program recorded in the storage device 86 on the program server 85 side, may be transmitted from the program server 85 side, and on the computer 81 side, the control program may be demodulated from the transmission signal received via the communications network 84, and the CPU may be made to execute the control program.

Furthermore, the present invention is not limited to the above described preferred embodiment, and various improvements and modifications can be made.

For example, in this preferred embodiment, the CPU 61 of the PC 30 executes the scope life display process when an input indicating an instruction to make the displaying unit 66 of the PC 30 display a scope history is given to the inputting unit 65 of the PC 30. Alternatively, the scope life display process may be executed when the CPU 61 of the PC 30 detects that a scope 10 is inserted in the endoscope system 20, or removed from the endoscope system 20. This enables the scope life display of the inserted/removed scope 10 to be immediately presented to its user, which is advantageous. Additionally, at this time, the scope use history screen shown in FIG. 9 for the scope 10 may be immediately displayed before the scope list screen shown in FIG. 8 is displayed. This enables the details of the history information 42 about the scope 10 to be presented to its user as well as the scope information 41 and the scope life display, which is convenient.

As described above in detail, according to the present invention, information about the use history of an endoscope is obtained, an estimation of a secular change in the endoscope from its use start until the present time is made, and the ratio of a result of the estimation to the degree of the secular change, which is preset for the endoscope, is displayed.

In this way, the result of the estimation of the secular change from the use start until the present time in an endoscope which changes monotonously is presented with the ratio to the degree of the secular change in the endoscope, which produces an effect that a margin remaining until the secular change in the endoscope becomes a predetermined degree can be suitably provided to a user of the endoscope.

What is claimed is:

1. A system providing information about an endoscope, comprising:
   a use time obtaining unit for obtaining a use time from a use start of an endoscope until a present time of use of the endoscope;
   a number of use times obtaining unit for obtaining a number of use times from the use start of the endoscope until the present time of use of the endoscope;
   an estimating unit making an estimation of a secular change in the endoscope from the use start until the present time based on the use time obtained by the use time obtaining unit and the number of use times obtained by the number of use times obtaining unit; and
   a displaying unit displaying a ratio of a result of the estimation to a degree of the secular change, which is preset for the endoscope, wherein
   the estimating unit determines a secular change amount of the endoscope as a result of the estimation, by adding a first secular change amount of the endoscope based on only the use time and a second secular change amount of the endoscope based on only the number of use times.

2. The system according to claim 1, wherein the degree of the secular change, which is preset for the endoscope, is a degree at which maintenance is recommended to be performed for the endoscope.

3. The system according to claim 1, wherein the information about the use time and the number of use times is stored in a scope storing unit comprised by the endoscope.

4. The system according to claim 3, wherein:
the scope storing unit further stores scope identification information for identifying the endoscope; and
the system further comprises a use history storing unit storing information about a use history of each of a plurality of endoscopes in association with the scope identification information.

5. The system according to claim 1, wherein said displaying unit displays the ratio of the result of the estimation as a figure.

6. The system according to claim 1, wherein said displaying unit individually displays the ratio of the result of the estimation of a plurality of endoscopes for each of the plurality of endoscopes.

7. The system according to claim 1, wherein said displaying unit lists and displays the ratio of the result of the estimation of each of a plurality of endoscopes.

8. A method providing information about an endoscope, comprising:
obtaining a use time from a use start of an endoscope until a present time of use of the endoscope;
obtaining a number of use times from the use start of the endoscope until the present time of use of the endoscope;
making an estimation of a secular change in the endoscope from the use start until the present time based on the obtained use time and the obtained number of use times; and
displaying a ratio of a result of the estimation to a degree of the secular change, which is preset for the endoscope, wherein
the making of the estimation determines a secular change amount of the endoscope as a result of the estimation, by adding a first secular change amount of the endoscope based on only the use time and a second secular change amount of the endoscope based on only the number of use times.

9. A computer-readable storage medium on which is recorded a program, by being executed by a computer, for causing the computer to execute a process for providing information about an endoscope, the process comprising:
obtaining a use time from a use start of an endoscope until a present time of use of the endoscope;
obtaining a number of use times from the use start of the endoscope until the present time of use of the endoscope;
making an estimation of a secular change in the endoscope from the use start until the present time based on the obtained use time and the obtained number of use times; and
displaying a ratio of a result of the estimation to a degree of the secular change, which is preset for the endoscope, wherein
the making of the estimation determines a secular change amount of the endoscope as a result of the estimation, by adding a first secular change amount of the endoscope based on only the use time and a second secular change amount of the endoscope based on only the number of use times.

10. A computer data signal embodied in a carrier wave and representing a program, by being executed by a computer, for causing the computer to execute a process for providing information about an endoscope, the process comprising:
obtaining a use time from a use start of an endoscope until a present time of use of the endoscope;
obtaining a number of use times from the use start of the endoscope until the present time of use of the endoscope;
making an estimation of a secular change in the endoscope from the use start until the present time based on the obtained use time and the obtained number of use times; and
displaying a ratio of a result of the estimation to a degree of the secular change, which is preset for the endoscope, wherein
the making of the estimation determines a secular change amount of the endoscope as a result of the estimation, by adding a first secular change amount of the endoscope based on only the use time and a second secular change amount of the endoscope based on only the number of use times.

11. A system providing information about an endoscope, comprising:
use time obtaining means for obtaining a use time from a use start of an endoscope until a present time of use of the endoscope;
a number of use times obtaining means for obtaining a number of use times from the use start of the endoscope until the present time of use of the endoscope;
estimating means for making an estimation of a secular change in the endoscope from the use start until the present time based on the use time obtained by the use time obtaining means and the number of use times obtained by the number of use times obtaining unit; and
displaying means for displaying a ratio of a result of the estimation to a degree of the secular change, which is preset for the endoscope, wherein
the estimating means determines a secular change amount of the endoscope as a result of the estimation, by adding a first secular change amount of the endoscope based on only the use time and a second secular change amount of the endoscope based on only the number of use times.

* * * * *